(12) United States Patent
Baum et al.

(10) Patent No.: US 7,032,431 B2
(45) Date of Patent: Apr. 25, 2006

(54) NON-INVASIVE, MINIATURE, BREATH MONITORING APPARATUS

(76) Inventors: Marc A. Baum, 2275 E. Foothill Blvd., Pasadena, CA (US) 91107; John A. Moss, 2275 E. Foothill Blvd., Pasadena, CA (US) 91107

( * ) Notice: Subject to any disclaimer, the term of this patent is extended or adjusted under 35 U.S.C. 154(b) by 24 days.

(21) Appl. No.: 10/864,808

(22) Filed: Jun. 8, 2004

(65) Prior Publication Data

US 2005/0054943 A1    Mar. 10, 2005

Related U.S. Application Data

(60) Provisional application No. 60/478,198, filed on Jun. 13, 2003.

(51) Int. Cl.
*G01N 1/22*    (2006.01)
*A61B 5/08*    (2006.01)

(52) U.S. Cl. .................................. 73/23.3; 600/532
(58) Field of Classification Search ................. 73/23.3; 600/532
See application file for complete search history.

(56) References Cited

U.S. PATENT DOCUMENTS

| | | | | |
|---|---|---|---|---|
| 4,648,396 A | * | 3/1987 | Raemer | 128/204.22 |
| 4,914,719 A | * | 4/1990 | Conlon et al. | 250/339.13 |
| 6,694,800 B1 | * | 2/2004 | Weckstrom et al. | 73/25.01 |

* cited by examiner

*Primary Examiner*—Daniel S. Larkin
(74) *Attorney, Agent, or Firm*—Trojan Law Office

(57) ABSTRACT

A means of miniaturizing the rugged, spectroscopic gas analyzer for rapid, non-invasive, multicomponent analysis of breath described in application Ser. No. 09/891,106, Filed on Jun. 25, 2001. A significant (ca. 4×) reduction in analyzer dimensions is achieved through a redesign of the optical bench: single detectors of IR radiation are replaced by detector arrays. A number of embodiments are discussed.

4 Claims, 6 Drawing Sheets

PRIOR ART

Front View　　　　　　Side View

NON-INVASIVE, MINIATURE, BREATH MONITORING APPARATUS

Priority of U.S. Provisional Application Ser. No. 60/478,198 filed Jun. 13, 2003 is hereby claimed.

BACKGROUND OF THE INVENTION

Background of the Invention

The provisional continuation application described here pertains to "A Non-invasive, Miniature, Breath Monitoring Apparatus", application Ser. No. 09/891,106, Filed on Jun. 25, 2001, incorporated herein by reference. Said application describes a spectroscopic gas analyzer for rapid, non-invasive, multicomponent analysis of breath and subsequent determination of cardiac output, or other useful physiological measurements. While the device is appropriate for clinical or out-patient (i.e., point-of-care) use in its current configuration, a number of specialized applications require an even smaller system. These include, but are not limited to:

"Mobile" human testing; device is carried by the human subject/patient (e.g., in backpack) during the test. This configuration allows freedom of motion, such as running, cycling, or other, Highly portable; for measurements in remote, inaccessible applications such as high altitude research, airplane or spacecraft missions (e.g., sustained microgravity research), military field clinics, screening of underserved civilian communities, especially in remote locations, home use, Integrated sensor suite; device is embedded with other sensors to form part of a package such as stress test equipment, ambulance diagnostics, Animal testing; device is strapped to animal subject for unimpeded diagnostic measurement. This is important as the animal cannot always be tested in the laboratory under controlled conditions. Examples of relevant applications include: cardiac output determination in race horses or dogs running on a track, or dolphins under water.

The continuation disclosed herein teaches a novel means of miniaturizing the technology from our application Ser. No. 09/891,106.

BRIEF DESCRIPTION OF THE INVENTION

The principal purpose of the disclosed invention consists of the quantitative analysis of gas-phase components of breath and the subsequent determination of cardiac output ($\dot{Q}$). This measurement is made non-invasively by using novel embodiments of spectroscopic gas sensing technology there-by facilitating further miniaturization than in the original disclosure. The present invention is unique in its optical design allowing multiple species to be monitored simultaneously to determine an accurate measure of $\dot{Q}$. The use of such an approach has not been reported previously to make $\dot{Q}$ measurements on subjects at rest or during exercise, nor any other form of breath analysis.

By making minor adjustments, the instrument is capable of measuring alternative analytes that may be of interest for $\dot{Q}$ monitoring (e.g., methane and Freon 22). The integration of an $O_2$ measurement channel allows the metabolic measurements to be carried out in conjunction with $\dot{Q}$ monitoring.

Similarly, the instrument has the capability of measuring numerous other gases, such as $NH_3$, $CO$, $N_2O$, ethanol, acetone, aldehydes, etc. for other biomedical applications, as described in our original application. Substitution of the standard four measurement channels (i.e., $CO_2$, $H_2O$, $C_2H_2$, and $SF_6$) with any of the above does not necessitate any software modifications and only requires minor hardware modifications (i.e., substitution of the optical filters).

The above and other objects, advantages, and novel features of the invention will be more fully understood from the following detailed description and the accompanying drawings, in which:

BRIEF DESCRIPTION OF THE DRAWINGS

The accompanying figures illustrate complete preferred embodiments of the present invention and the best modes presently devised for the practical application of the principles thereof, in which.

DESCRIPTION OF THE PREFERRED EMBODIMENTS

Figure 1:
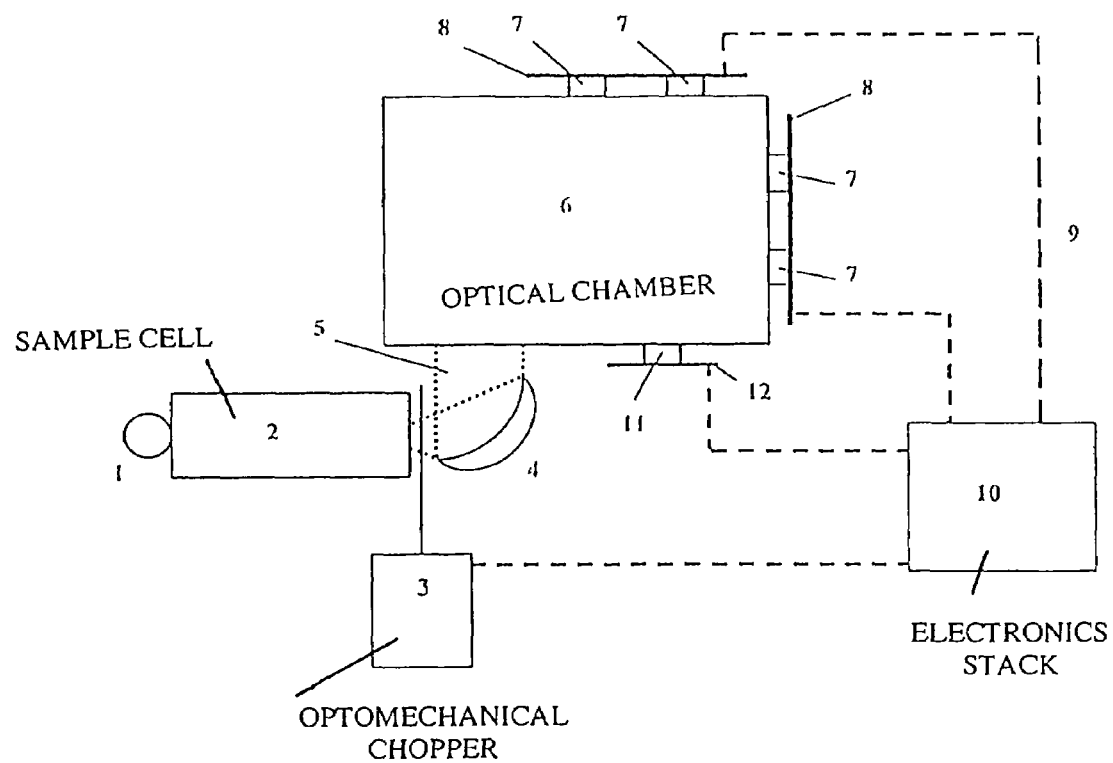
FIG. 1. Schematic representation of the disclosed invention.

A typical embodiment of the invention disclosed in application Ser. No. 09/891,106, filed on Jun. 25, 2001 is shown schematically in FIG. 1. In summary, radiation from emitter (1) is collected by miniature sample cell (2) (the emitter is said to be "butt-coupled" to the sample cell), where sample cell (2) consists of a low volume light pipe. The breath sample to be analyzed is continuously aspirated through sample cell (2). The radiation exiting the sample cell is modulated by optomechanical chopper (3) and collected by optic (4), which can consist of an off-axis parabolic reflector, collimated by optic (4) and projected into optical chamber (6). The modular design of optical chamber (6) made up one of the novel features of application Ser. No. 09/891,106 incorporated by reference and is discussed in detail therein. In summary, collimated beam (5) is partitioned to a plurality of detectors (7) and (11) by means of suitable beamsplitters, mirrors, and lenses. Each detector is equipped with a narrow bandpass optical filter (NBOF)—not shown—which isolates the appropriate spectral window to make the measurement of the corresponding analyte (see application Ser. No. 09/891,106 for a detailed explanation). The signals from the detectors are amplified and conditioned by pre-amplifier boards (8) and (12), and analog signal (9) is relayed to computer and electronics stack (10), where the signals are conditioned further and digitized. The invention disclosed herein concerns miniaturization of optical chamber (6).

Figure 2A:
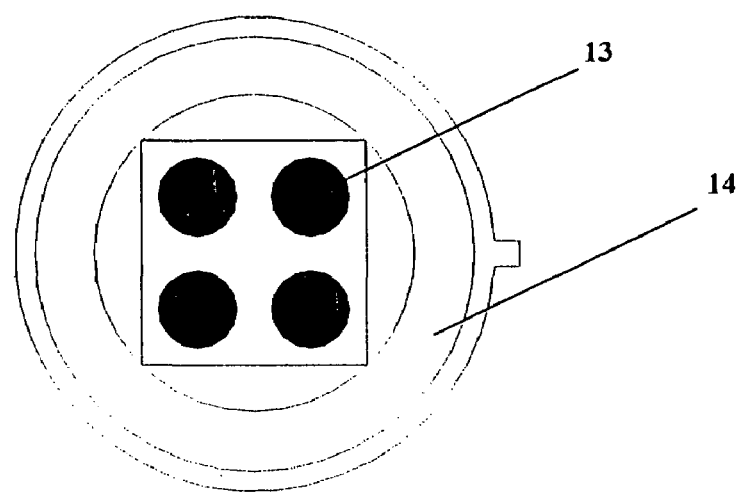
FIG. 2. Drawing of lead-salt detector array.
Figure 2B:
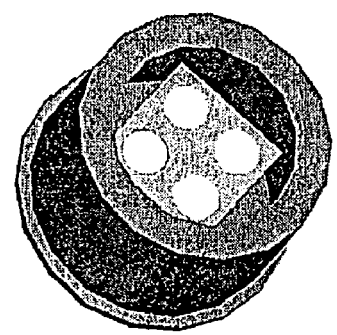

One embodiment of the disclosed invention is motivated by the recent availability (e.g., SensArray Corporation, Burlington, Mass.) of small lead-salt (e.g., lead sulfide, PbS, and lead selenide, PbSe) arrays that do not require cryogenic cooling to respond sensitively to infrared (IR) radiation appropriate for measuring the compounds of interest for breath analysis (see application Ser. No. 09/891,106); i.e., in the 1.0–6.0 μm wavelength range. These arrays only include a small number of elements, say 2–16, and can be custom-engineered with the appropriate mask for a wide range of pixel sizes and geometries. FIG. 2A illustrates a four-element array (front view), where each detector (13) is symmetrically distributed in a standard electronics package (14). A 3-D representation is given in FIG. 2B.

Figure 3:
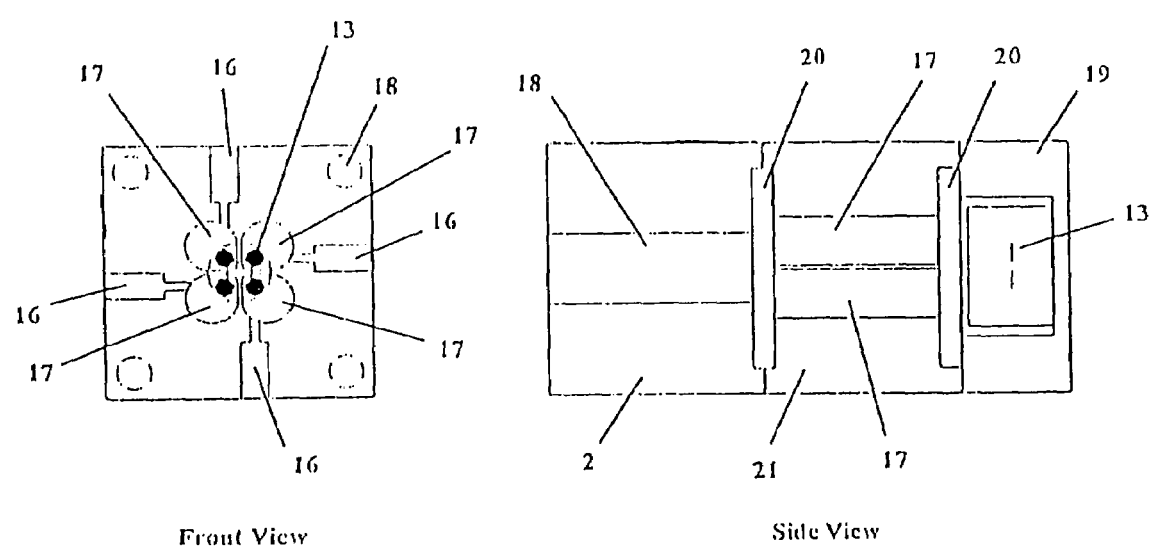
FIG. 3. Optical layout of the disclosed invention interfaced with 4-element detector array.
Figure 4A:
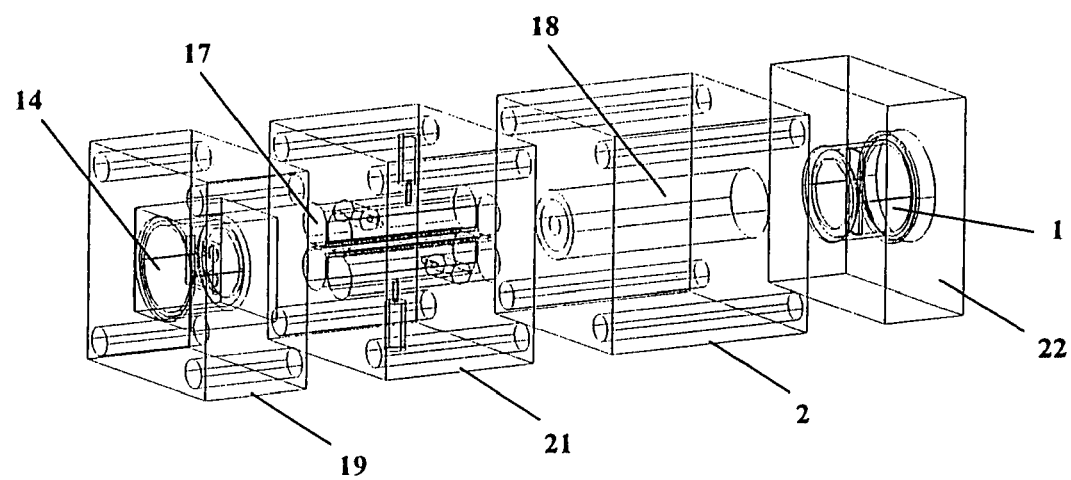
FIG. 4. Three-dimensional representation of light pipe-gas cell-detector array assembly.
Figure 4B:
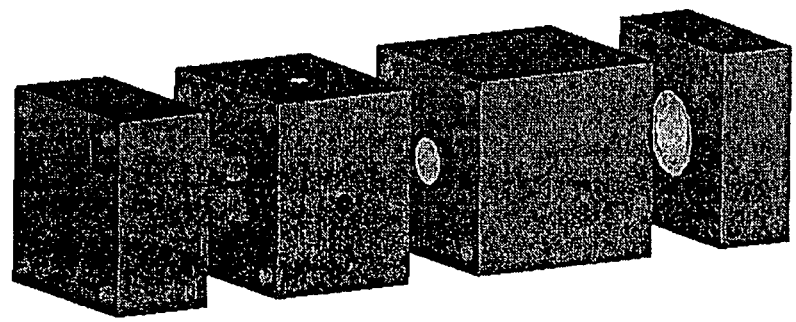

FIG. 3 schematically illustrates a preferred embodiment of the invention where the light pipe (2) bolts directly to gas filter correlation cell (21), which, in turn, bolts directly to detector heat sink (19). Cell (21) is isolated from (2) and (19) via a pair of optical windows (20). Another window—not shown—at the other end of light pipe (2) seals low volume conduit (18) from the sample stream aspired continuously from the human/animal subject being tested. Gas cell (21) consists of four independent chambers (17) that can be filled with a suitable gas filter correlation (GFC) gas via ports (16). Gases of interest to breath analysis commonly measured by GFC spectroscopy include $C_2H_2$, $CH_4$, CO, $N_2O$, etc. (see application Ser. No. 09/891,106 for further details). When GFC is not employed, chambers (17) can be filled with room air, $N.sub.2$, argon, or can be sealed under vacuum. Each detector element (13) of the array can be apertured by a different gas cell and NBOF using this simple approach. A 3-D representation of the assembly shown in FIG. 3 is shown in FIGS. 4A and 4B and further teaches how such a novel optical chamber can be configured. FIGS. 4A and 4B also show optical block (22), which houses IR source (1). Note that a gap may be required for the blade of optomechanical chopper (3); in many cases a chopper is not required as the array can be integrated/gated electronically. FIGS. 4A and 4B also illustrate the modular nature of the design. Optomechanical blocks (2), (19), (21), and (22) can conveniently and economically be machined out of aluminum. This novel miniature assembly also has the advantage of being very economically attractive, as many optical elements used in the original design (see application Ser. No. 09/891,106) can be omitted. The inherent simplicity of the design also makes it very robust.

Figure 5:
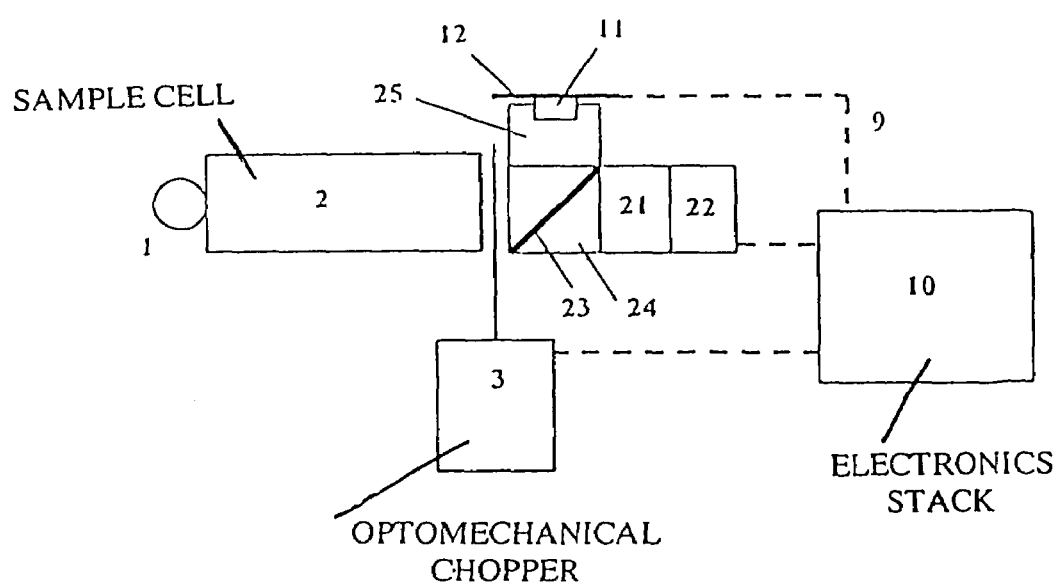
FIG. 5. Optomechanical layout of the disclosed invention, using a four-detector mid-IR array in conjunction with one far-IR detector.

The approach used in FIGS. 3 and 4A and 4B can be employed to monitor a wide range of breath gases, including, but not limited to, the following combinations:

Four mid-IR detector system for $\dot{Q}$ monitoring; $C_2H_2$ reference (GFC compartment filled with $C_2H_2$), $C_2H_2$ sample (GFC compartment filled with $N_2$), $CO_2$ reference (GFC compartment filled with $N_2$), $CO_2$ sample (GFC compartment filled with $N_2$). This approach also requires far-IR detector (11) for $SF_6$ monitoring (see application Ser. No. 09/891,106), as illustrated schematically in FIG. 5, where beamsplitter (23) reflects the long wavelength IR radiation through optical block (25), Six mid-IR detector system for $\dot{Q}$ monitoring; $C_2H_2$ reference (GFC compartment filled with $C_2H_2$), $C_2H_2$ sample (GFC compartment filled with $N_2$), $CO_2$ reference (GFC compartment filled with $N_2$), $CO_2$ sample (GFC compartment filled with $N_2$), $CH_4$ reference (GFC compartment filled with $CH_4$), $CH_4$ sample (GFC compartment filled with $N_2$). This configuration does not require a far-IR detector, as $CH_4$ is used in lieu of $SF_6$ as the blood-insoluble gas, Four mid-IR detector system for CO pulmonary diffusive capacity monitoring; CO reference (GFC compartment filled with CO), CO sample (GFC compartment filled with $N_2$), $CH_4$ reference (GFC compartment filled with $CH_4$), $CH_4$ sample (GFC compartment filled with $N_2$).

This configuration does not require a far-IR detector, as $CH_4$ is used in lieu of $SF_6$ as the blood-insoluble gas, Six mid-IR detector system for $\dot{Q}$ and CO pulmonary diffusive capacity monitoring; $C_2H_2$ reference (GFC compartment filled with $C_2H_2$), $C_2H_2$ sample (GFC compartment filled with $N_2$), $CO_2$ reference (GFC compartment filled with $N_2$), $CO_2$ sample (GFC compartment filled with $N_2$), CO reference (GFC compartment filled with CO), CO sample (GFC compartment filled with $N_2$). This approach also requires far-IR detector (11) for $SF_6$ monitoring (see application Ser. No. 09/891,106), as illustrated schematically in FIG. 5, where beamsplitter (23) reflects the long wavelength IR radiation through optical block (25).

Note that $N_2O$ can be substituted directly for $C_2H_2$, where desired, as the blood-soluble gas. Many other permutations are possible due to the modular nature of the design.

In another preferred embodiment of the disclosed invention, GFC cell assembly (21) and detector array assembly (22) are replaced entirely by a dispersive mid-IR spectrometer including a linear array, consisting of a plurality, typically 128 or more, of detectors. Examples of suitable array detectors for IR measurements include: pyroelectric and thermopile array systems, as supplied by Ion Optics, Inc. (Waltham, Mass.), multiplexed lead sulfide and lead selenide arrays Textron Systems (Petaluma, Calif.) and/or Litton Electro-Optical Systems (Tempe, Ariz.) and/or SensArray Corporation (Burlington, Mass.) would be suitable. Other detector arrays, such as mercury cadmium telluride, supplied by Cincinnati Electronics Corp. (Mason, Ohio), and indium antimonide, supplied by Litton Electro-Optical Systems (Tempe, Ariz.), could also be used for IR measurements The array, which needs to have a response time below 30 ms, is optically interfaced with a grating, such as a holographic grating, which disperses the broadband radiation into its component wavelengths without the need for moving mechanical parts using a standard spectrometer design (e.g., Czerny-Turner). This allows spectra to be processed to extract analyte concentrations using standard methods (see Baum, M. M.; Lord, H. C. Spectroscopic Remote Sensing Exhaust Emission Monitoring System. U.S. Pat. No. 6,455,851, Sep. 24, 2002). In one preferred embodiment of the disclosed invention, a mid-IR spectrometer (e.g., using a PbSe array) is used in conjunction with a far-IR $SF_6$ detector in an analogous fashion to the configuration shown in FIG. 5. When an array is used with sensitivity in the far-IR, (e.g., mercury cadmium telluride), all analytes of interest may be monitored in the dispersive spectrometer. Alternatively, $CH_4$ can be used in lieu of $SF_6$ as the blood-insoluble gas and all analytes of interest can be monitored in the mid-IR spectrometer.

Figure 6:
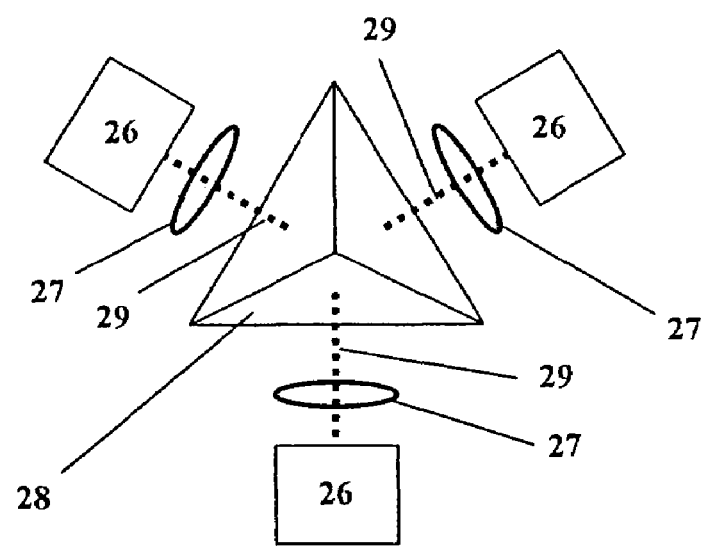
FIG. 6. Prism-based beam combiner.

Finally, FIG. 6 shows a preferred embodiment of the disclosed invention for combining the emission from a plurality of IR sources (26) including, but not limited to:

Pulsable broadband emitter (e.g., SVF360-8M, CalSensors, NL8LNC, Ion Optics, Waltham, Mass.), IR light emitting diode (LED) (suppliers include: Institute of Semiconductor Physics, Nauky, Ukraine, Telcom Devices Corporation, Camarillo, Calif., Physico-Technical Institute, St. Petersburg, Russia, Laser Monitoring Systems Ltd., Devon, England), Superluminescent diode (Sarnoff Corporation, Princeton, N.J.), Narrow-band semiconductor incandescent source (Ion Optics), Tunable diode laser, a tunable quantum cascade laser, a pulsed miniature $CO_2$ laser, such as LASY-1 manufactured by Access Laser Co. (Marysville, Wash.), Any other emitter of radiation that can be electronically pulsed.

The output from the IR emitted is collimated using suitable optics (27) and the resulting beams (29) are combined using (optically coated) prism (28). The combined beam traverses light pipe (2) and can be analyzed with the optical chamber(s) disclosed in the original application, or with any of the embodiments discussed above. This embodiment does not require chopper (3) as all beams are already electronically modulated/pulsed.

This invention is not to be limited by the embodiment shown in the drawings and described in the description which is given by way of example and not of limitation, but only in accordance with the scope of the appended claims.

What is claimed is:

1. A miniaturized breath monitoring system comprising:
   a radiation emitter;
   a miniature sample cell receiving a breath sample to be analyzed receiving an input from said radiation emitter;
   a modulator for modulating radiation exiting from said miniature sample cell;
   an optic collector for collecting modulated radiation being projected as a collimated beam into an optical chamber;
   said optical chamber partitioning said collimated beam to a plurality of detectors;
   each of said detectors being equipped with a narrow bandpass optical filter for isolating an appropriate spectral window to measure a corresponding analyte and
   a plurality of pre-amplified boards receiving and conditioning output signals from said optical detectors;
   whereby said optical chamber may be minimized wile producing an accurate breath analysis.

2. The system according to claim 1 in which said radiation emitter is butt-coupled to said miniature sample cell; said sample cell comprising a low volume light pipe.

3. The system according to claim 2 in which said modulator is an optomechanical chopper.

4. The system according to claim 3 in which said optic collector collecting said radiation from said modulator is an off-axis parabolic reflector, collimating and projecting said sample into said miniaturized optical chamber.

* * * * *